(12) United States Patent
Karakelle et al.

(10) Patent No.: US 8,821,572 B2
(45) Date of Patent: Sep. 2, 2014

(54) INTRAOCULAR LENS DELIVERY DEVICE HAVING A CARTRIDGE WITH AN INTERNAL COATING

(75) Inventors: Mutlu Karakelle, Fort Worth, TX (US); David A. Downer, Fort Worth, TX (US); Sushant Muchhala, Kennedale, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 269 days.

(21) Appl. No.: 12/620,639

(22) Filed: Nov. 18, 2009

(65) Prior Publication Data

US 2010/0125279 A1 May 20, 2010

Related U.S. Application Data

(60) Provisional application No. 61/116,443, filed on Nov. 20, 2008.

(51) Int. Cl.
*A61F 2/16* (2006.01)

(52) U.S. Cl.
CPC .................................. *A61F 2/1678* (2013.01); *A61F 2/1675* (2013.01)
USPC ........................................ 623/6.12; 606/107

(58) Field of Classification Search
CPC ........................................ A61F 2/1662–2/1691
USPC ........................................ 606/107; 623/6.12
See application file for complete search history.

(56) References Cited

U.S. PATENT DOCUMENTS

| 4,681,102 | A | | 7/1987 | Bartell |
| 5,272,012 | A | | 12/1993 | Opolski |
| 5,275,604 | A | | 1/1994 | Rheinish et al. |
| 5,494,484 | A | | 2/1996 | Feingold |
| 5,499,987 | A | | 3/1996 | Feingold |
| 5,599,576 | A | | 2/1997 | Opolski |
| 5,616,148 | A | | 4/1997 | Eagles et al. |
| 5,620,450 | A | | 4/1997 | Eagles et al. |
| 5,653,715 | A | | 8/1997 | Reich et al. |
| 5,776,158 | A | | 7/1998 | Chou |
| 5,776,611 | A | | 7/1998 | Elton et al. |
| 5,803,925 | A | * | 9/1998 | Yang et al. ............. 606/107 |
| 5,947,976 | A | | 9/1999 | Van Noy et al. |

(Continued)

FOREIGN PATENT DOCUMENTS

| JP | 2000507997 | 6/2000 |
| JP | 2005219469 | 8/2005 |

(Continued)

OTHER PUBLICATIONS

PCT International Search Report for corresponding PCT/US2009/064882 with mailing date Feb. 24, 2010.

(Continued)

*Primary Examiner* — Kathleen Holwerda
*Assistant Examiner* — Sarah W Aleman
(74) *Attorney, Agent, or Firm* — Scott A. Chapple

(57) ABSTRACT

An intraocular lens (IOL) delivery device is disclosed. The device includes an intraocular lens cartridge having an internal coating wherein the coating includes a polymeric material that is compatible with a polymeric material of a material that forms the cartridge. Preferably, the polymeric material of the coating, the cartridge or both is a polyurethane material.

21 Claims, 1 Drawing Sheet

(56) References Cited

U.S. PATENT DOCUMENTS

| | | | |
|---|---|---|---|
| 6,004,300 A * | 12/1999 | Butcher et al. | 604/222 |
| 6,096,076 A * | 8/2000 | Silvestrini | 623/5.12 |
| 6,096,726 A | 8/2000 | Opolski | |
| 6,238,799 B1 * | 5/2001 | Opolski | 428/423.1 |
| 6,428,501 B1 * | 8/2002 | Reynard | 606/107 |
| 6,683,062 B2 | 1/2004 | Opolski | |
| 6,866,936 B2 | 3/2005 | Opolski | |
| 7,494,505 B2 * | 2/2009 | Kappelhof et al. | 623/6.12 |
| 2005/0065534 A1 | 3/2005 | Hohl | |
| 2005/0277944 A1 | 12/2005 | Kappelhof et al. | |
| 2006/0229635 A1 | 10/2006 | Hu et al. | |
| 2007/0005135 A1 | 1/2007 | Makker et al. | |
| 2007/0052923 A1 | 3/2007 | Ayyagari et al. | |
| 2008/0027461 A1 * | 1/2008 | Vaquero et al. | 606/107 |
| 2009/0155595 A1 * | 6/2009 | Lee | 606/107 |

FOREIGN PATENT DOCUMENTS

| | | |
|---|---|---|
| JP | 200721010 | 2/2007 |
| JP | 2007021010 | 2/2007 |
| JP | 2008535632 | 9/2008 |
| WO | 9409048 | 4/1994 |
| WO | 2004014259 A1 | 2/2004 |
| WO | 2006110696 A1 | 10/2006 |

OTHER PUBLICATIONS

PCT International Written Opinion for corresponding PCT/US2009/064882 with mailing date Feb. 24, 2010.

* cited by examiner

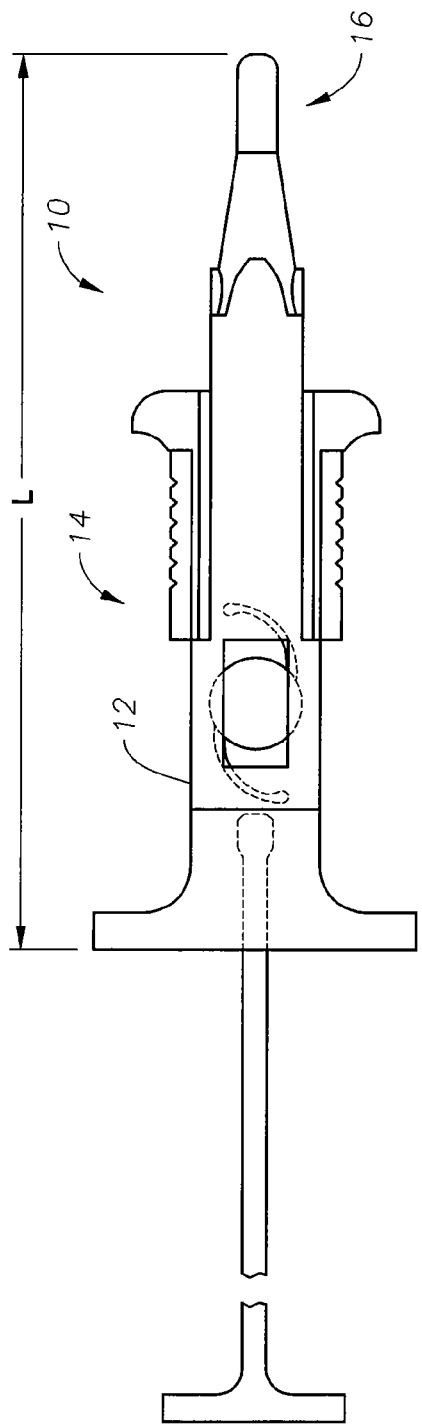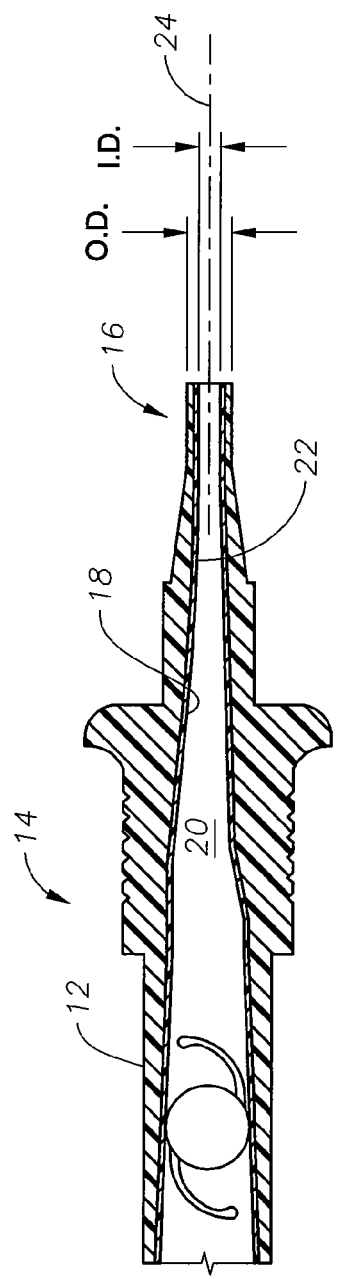
Fig. 1
Fig. 2

INTRAOCULAR LENS DELIVERY DEVICE HAVING A CARTRIDGE WITH AN INTERNAL COATING

CROSS REFERENCE TO RELATED APPLICATION

This application claims priority under 35 U.S.C. §119 to U.S. Provisional Patent Application No. 61/116,443, filed Nov. 20, 2008, the entire contents of which are incorporated herein by reference.

TECHNICAL FIELD OF THE INVENTION

The present invention is related to an intraocular lens cartridge having an internal coating wherein the coating includes a polymeric material that is compatible with a polymeric material of a material that forms the cartridge.

BACKGROUND OF THE INVENTION

The human eye functions to provide vision by transmitting and refracting light through a clear outer portion called the cornea, and further focusing the image by way of a lens onto the retina at the back of the eye. The quality of the focused image depends on many factors including the size, shape and length of the eye, and the shape and transparency of the cornea and lens.

When trauma, age, disease or otherwise cause an individual's natural crystalline lens to become less transparent, vision deteriorates because of the diminished light which can be transmitted to the retina. This deficiency in the lens of the eye is often referred to as a cataract. The treatment for this condition is surgical removal of the natural crystalline lens and implantation of an intraocular lens (IOL).

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. One commonly used injector cartridge design is illustrated in U.S. Pat. No. 4,681,102 (Bartell), and includes a split, longitudinally hinged cartridge. Similar designs are illustrated in U.S. Pat. Nos. 5,494,484 and 5,499,987 (Feingold) and U.S. Pat. Nos. 5,616,148 and 5,620,450 (Eagles, et al.), the entire contents of which are incorporated herein by reference. Still other cartridges are described in U.S. Pat. No. 5,275,604 (Rheinish, et al.), U.S. Pat. No. 5,653,715 (Reich, et al.) and U.S. Pat. No. 5,947,876 (Van Noy, et al.), the entire contents of which are incorporated herein by reference.

As an IOL is pushed by a plunger through a small diameter lumen of the cartridge, relatively large amounts of force can be placed upon the plunger, the cartridge and/or the IOL. Generally, it is desirable to have the cartridge manage these forces to promote effective delivery of an IOL. These forces have recently become an increasing concern. In particular, the medical community has expressed a desire for IOL cartridges to have smaller nozzles, which in turn allows a surgeon to use a smaller incision for delivery of an IOL to an individual's eye. These smaller nozzles result in smaller lumens through which the IOL must be pushed during IOL delivery. Therefore, the forces placed on the IOL, the cartridge nozzle and the plunger during delivery of the IOL can be significantly increased and management of these forces can be challenging.

To alleviate forces that occur during IOL delivery, low friction coatings are often applied to the internal surface of the cartridges to allow the IOL to more easily pass through the lumen defined by that internal surface. However, conventional coatings for IOL cartridges can be complex to apply and can involve multiple layers and multiple different materials. In turn, such coatings can be difficult to apply in a consistent manner and can take up space of the lumen through which the IOL would normally pass.

In addition to coatings, management of IOL delivery forces can also be accomplished through the use of materials that are capable of handling those forces, particularly materials for the delivery cartridge. However, it is extremely challenging to find a material that is suitable for insertion into any eye and exhibits the desired physical properties for handling IOL delivery forces while, at the same time, is compatible with a coating that is to be applied to an internal surface of the IOL delivery cartridge.

In view of the above, it would be desirable to provide an IOL cartridge and coating combination where the coating is improved relative to conventional coatings and the material that forms the cartridge is compatible with the improved coating while still exhibiting desirable physical properties.

SUMMARY OF THE INVENTION

Accordingly, the present invention is directed to an IOL delivery device. The device includes a delivery cartridge having a body portion and a nozzle, the body portion and nozzle including an internal surface defining a lumen extending along the body portion and the nozzle. The internal surface is formed of polymeric material that is either a polyurethane material or a non-olefinic polymeric material having a heterogeneous backbone. A coating is disposed over the internal surface and the coating is formed of a polyurethane material and a hydrophilic material.

The polyurethane material of the coating forms a cross-linked or linear matrix and the hydrophilic material is dispersed throughout the matrix. It is preferable for the coating to be a single layer disposed directly over the internal surface of the cartridge without any coating layers over the single layer, although other configuration may be possible.

It is also preferred, although not required unless otherwise stated, for the cartridge and the internal surface to be formed of a singular polymeric material. The material of the internal surface typically exhibits a flexural modulus that is at least 200 MPa, more typically at least 1200 MPa and even more typically at least 2000 MPa. Further, the material of the internal surface typically exhibits a hardness of at least 50D, more typically at least 75D and even possibly at least 90D.

BRIEF DESCRIPTION OF THE DRAWING

FIG. 1 is a drawing of an exemplary IOL delivery device in accordance with an aspect of the present invention.

FIG. 2 is a sectional view of a portion of the IOL delivery device of FIG. 1.

DETAILED DESCRIPTION OF THE INVENTION

The present invention is predicated upon the provision of an IOL delivery device that includes a delivery cartridge formed of a material and a coating that is compatible with that material. The material of the delivery cartridge preferably exhibits physical properties that are desirable for accommodating forces that occur during the delivery an IOL through the cartridge. Moreover, the compatibility between the material of the cartridge and the coating may allow for ease of coating application. Generally, the material of the cartridge is a polymeric material that is from the same family as a polymeric material of the coating or otherwise exhibits an affinity for the material of the polymeric material. In a preferred embodiment, the cartridge and the coating (e.g., a matrix forming material of the coating) are both formed of a polyurethane material.

With reference to FIG. 1, there is illustrated an exemplary IOL delivery device 10 that includes a cartridge 12 having a body portion 14 and a nozzle 16. The cartridge 12, particularly the body portion 14 and the nozzle 16, define an internal surface 18 that defines a lumen 20 extending along a length (L) of the cartridge 12, the body portion 14 and the nozzle 16. The internal surface 18 is covered by a coating 22 according to the present invention. The nozzle 16 is typically configured to be insertable into an incision in an eye to aid in the delivery an IOL through the nozzle 16 into the eye. As can be seen, the nozzle 16 has an inner diameter (ID) and an outer diameter (OD) taken perpendicular to an axis 24 extending along a length of the nozzle such axis being the same as the length (L) shown in FIGS. 1-3. It is preferable, although not required unless otherwise stated, that inner diameter, the outer diameter or both of the nozzle 16 be less than 6 millimeter (mm), more typically less than 3 mm, still more typically less than 2.5 mm and even possibly less than 1.9 mm.

The cartridge can generally be formed of a variety of polymeric materials and may be formed of a singular polymeric material or multiple polymeric materials. When multiple polymeric materials are employed, they may be in layers or intermixed. Examples of potential polymeric materials include, without limitation, polyurethanes, polycarbonates, polysulphones, polyetherimides, polyether block amides, polypropylenes, polyacrylates and polymethacrylates, polyethylene or polypropylene copolymers, polyvinyl chloride, epoxides, polyamides, polyesters or copolymers with rubbers, siloxanes or other polymers, combinations thereof or the like.

It is generally preferable that the material forming the cartridge and/or the internal surface of the lumen be relatively hydrophilic and exhibits a desired water contact angle for making the material more compatible with a matching polymeric material of the coating, which is preferably a polyurethane material. Such contact angle is typically at least 50°, more typically at least 70° and even more typically at least 75°. Such contact angle is also typically less than 85° and more typically less than 80°. Contact angle can be measured for the present invention using Sessile drop contact angle measurement techniques.

The material of the cartridge that receives the coating is preferably substantially or entirely non-polyolefinic. This means that the material forming the is cartridge and/or forming the internal surface of the lumen of the cartridge includes less than 50%, more typically less than 30%, even more typically less than 20% and even possibly less than 5% by weight of any polyolefin, particularly polypropylene and polyethylene and, in one preferred embodiment is entirely without any polyolefin. It is generally preferable that the material forming the cartridge and/or forming the internal surface of the lumen of the cartridge be a polyurethane material (i.e., a material that includes a substantial portion of polyurethane). As use herein, the inclusion of a substantial portion of polyurethane means the inclusion of at least 20% more typically at least 40% and possibly at least 70% by weight polyurethane.

The polyurethane material of the cartridge and/or the internal surface of the lumen can be formed entirely or substantially entirely of polyurethane without any other polymer type blended or copolymerized therewith. Alternatively, the polyurethane material can be a blend a polyurethane and one or more other polymers or a copolymer of polyurethane and one or more other polymers. It is generally preferred that the thermoplastic material be entirely or substantially entirely thermoplastic, although not necessarily required unless otherwise stated. Exemplary copolymers can include, without limitation, polyurethane/polyether copolymers, polyester/polyurethane copolymers, combinations thereof or the like.

Exemplary suitable polyurethane materials include rigid thermoplastic urethanes sold under the tradenames ISOPLAST® 2531 and ISOPLAST® 2530, which are commercially available from The Dow Chemical Company, Midland, Mich. Another exemplary suitable polyurethane material is a thermoplastic polyurethane elastomer, which may be a copolymer. Examples of such polyurethane material are polyether based polyurethane materials, which are often aliphatic and which are sold under the tradenames PELLETHANE® 2362 75D and PELLETHANE® 2363 65D, which are also commercially available from The Dow Chemical Company, Midland, Mich. Other suitable thermoplastic polyurethane copolymers include, without limitation, aromatic polyether/polyurethane copolymers, polycaprolactam copolyester/polyurethane copolymers or the like. It is also contemplates that combinations of any of the aforementioned polymeric materials may also be employed as the material for the cartridge.

Although, the material of the cartridge and the surface defining the lumen is preferably a polyurethane material, it is contemplated that other materials may be used where those materials have properties similar to polyurethanes and therefore exhibit a similar affinity for the coating. Such materials will typically have water contact angles as described herein. Moreover, such material will typically be polymers with heterogeneous backbones and those backbones will typically include both carbon and oxygen atoms in their monomers, oligomers or both. Polycarbonates are good examples of these alternative materials. Another suitable example includes polyether amide copolymer such as those sold under the tradename PEBAX®, which are commercially available from Arkema having an address at 420, rue d'Estienne d'Orves, F-92705 Colombes Cedex France.

For use as an IOL delivery cartridge, it is desirable for the material of the cartridge to have a desired flexural modulus and desired hardness. Typically, the flexural modulus will be at least 200 MPa, more typically at least 1200 MPa and even more typically at least 2000 MPa. The flexural modulus will typically be less than 5000 MPa, more typically less than 3000 MPa and even more typically less than 2600 MPa. The flexural modulus can be measured in accordance with ASTM D790. Typically, the hardness will be at least 50D, more typically at least 75D and even possibly at least 90D. The hardness will typically be less than 120D, more typically less than 100D and even possibly less than 95D. The hardness can be measured in accordance with ASTM D2240 Standard Test Method for Rubber Property-Durometer Hardness.

It is preferable that the material of the coating 22 include a substantial portion of a polymeric material that matches (i.e., is from that same family of) the polymeric material that forms the internal surface 18 of the cartridge 12. In particular, it is preferable that the matching materials (i.e., the polymeric material of the coating and the polymeric material that forms the internal surface 18 of the cartridge 12) have at least 70%, more preferably at least 90% the same monomeric repeat units, oligomeric repeat units or both. Alternatively or additionally, the matching materials can be composed of at least 70%, more preferably at least 90% urethane structures.

The polymeric material of the coating that matches the polymeric material of the internal surface of the cartridge is preferably at least 30%, more typically at least 40% and even more typically at least 45% by weight of the coating material once the coating material has been applied and dried. The polymeric material is also typically no greater than about 90%, more typically no greater than about 80% and even more typically no greater than about 60% by weight of the coating material once the coating material has been applied and dried. It is possible that this matching polymeric material can be from any of the families discussed in relation to the material of the cartridge. Preferably, the matching polymer material is a polyurethane material.

The polyurethane, when used, will typically have particular properties prior to incorporation into the coating. The polyurethane will typically have a viscosity at 23° C. of at least about 50 centipoise (cps), more particularly at least 100 cps. The viscosity of the polyurethane at 23° C. is typically no greater than about 390 cps and more typically no greater than about 250 cps. The polyurethane will also typically have a solids content between about 30 and 50 and more particularly between about 35 and 41. The polyurethane will also typically have a pH that is between about 6.0 and about 10 and more preferably between about 7.5 and about 9.0.

In a preferred embodiment, the coating includes the polymeric matching material, a hydrophilic material and, optionally, a cross-linking agent or cross-linker. In such embodiment, the polymeric matching material is typically cross-linkable to form a matrix suitable for assisting in retaining the hydrophilic material. Examples of such coatings are provided in U.S. Pat. No. 6,238,799, which is incorporated herein by reference for all purposes. Another example of a suitable coating is sold under the tradename LUBRILAST® and is commercially available from Advanced Surface Technologies, 9 Linnell Circle, Billerica, Mass. 01821.

The hydrophilic material is typically a polymer which swells in the presence of water to provide a "slippery" or lubricous surface. Exemplary hydrophilic polymers include, but are not limited to, poly(N-vinyl lactams, such as poly (vinylpyrrolidone) (PVP) and the like, poly(ethylene oxide) (PEO), poly(propylene oxide) (PPO), polyacrylamides, cellulosics, such as methyl cellulose and the like, polyacrylic acids, such as acrylic and methacrylic acids and the like, polyvinyl alcohols, and polyvinyl ethers and the like.

The ratio of polymeric matching material (e.g., polyurethane) to hydrophilic polymer in the coating, by weight, is typically between about 10:1 and about 1:10, more typically between about 5:1 and about 1:5, still more typically between about 2:1 and about 1:2 and even still more typically between about 1.3:1 and about 1:1.3.

In a particularly preferred embodiment, the hydrophilic material is or includes PVP. The PVP may have one or a mixture of K values from K15 or possibly lower to K90 or possibly higher. Preferred PVPs have a K value between about 80 and 110. The PVP typically has an average molecular weight that is at least about 500,000 Daltons, more typically at least 800,000 Daltons and even more typically at least 1.0 M Daltons. The molecular weight of the PVP is also typically less than about 3.0 M Daltons, more typically less than about 1.8 M Daltons and even more typically less than about 1.4 M Daltons.

The crosslink reaction of the matching polymeric material of the coating may be self-initiating so that functional groups of the polymer themselves form the crosslink. Suitable functional groups capable of self-crosslinking include, but are not limited to, alkyd oxidatively drying resins, formaldehyde condensates, methyol acrylamides and allylic groups. Such crosslinking may be initiated by application of heat or UV energy, for example. Heating up to 150° C. or more may be used.

In other embodiments, the crosslink reaction may be initiated by addition of a crosslink agent to the coating composition. Such crosslinking agent may be added to the coating composition immediately prior to the coating operation. Alternatively, the coated article may be exposed to the crosslinking agent after coating, such as, by way of example, swelling of a dry coating in an aqueous solution containing the crosslinking agent. Suitable crosslinking agent include, but are not limited to, polyfunctional aziridines, polyfunctional carbodiimides and polyfunctional epoxides. Typically, the crosslinking agent is a di- or tri-functional compound; however, it is contemplated as being within the scope of the invention to use polyfunctional crosslink agents having any number of functional groups. The crosslinking agent may form one or more crosslinks with the supporting polymer and/or crosslinking with adjacent crosslink agent. The crosslink agent may additionally react with active substrate moieties on the IOL cartridge surface, especially if the functional groups are generated on the surface by pretreatment of the surface to expose functional groups. This results in a higher crosslink density for the hydrophilic polymer, which may be desirable in some instances, for example, where the hydrophilic polymer is of lower molecular weight, has a poorer affinity for the supporting polymer than desired or where the supporting polymer possesses a low level of functional moieties.

The IOL cartridge can be formed using various polymer molding or shaping techniques. Examples include, without limitation, compression molding or injection molding (e.g., thermoplastic injection molding or reaction injection molding). The surface of the cartridge to be coated with the coating may be treated (e.g., plasma treated) to provide that surface with reactive groups, which are discussed above. In a preferred embodiment, the cartridge, including the internal surface defining the lumen, is injection molded of a singular continuous material.

The coating is typically formed by combining the matching polymeric material with the hydrophilic material and, optionally the cross-linking agent, in an aqueous or other medium. In a preferred embodiment, the matching polymeric material and the hydrophilic material are both separately provide in aqueous mediums and are mixed together in a container (e.g., a flask or beaker) with a mixing bar to form an admixture. The cross-linking agent is then mixed into this admixture shortly before application of the coating to the IOL cartridge.

The coating may be applied to the internal surface of the lumen of the cartridge using various techniques. For example, the coating may be dip coated, swabbed, brushed or otherwise applied. In one preferred embodiment, injection devices such as needles are used to fill the internal lumen of the cartridge with the coating material at areas such as the nozzle and areas adjacent the nozzle along which an IOL will travel during delivery. In this manner, the coating is allowed to associated with (i.e., adhere and/or react with) the internal surface of the lumen. The extra coating is then purged (i.e., drained) from the cartridge. Thereafter, the coating is allowed to dry through heating and/or water evaporation.

The coating typically provides a surface that can receive and retain water and, in turn, provide a lubricious surface. An IOL can then relatively easily slide across the coated surface during delivery thereof. This is particularly advantageous for delivery of softer IOLs that are being delivered through a relatively narrow lumen. Thus, the delivery system is quite desirable for delivery of hydrophobic acrylic foldable IOLs into the eye of an individual.

Advantageously, when polyurethane and particularly the polyurethane copolymer material or polycarbonate is used as the material of the cartridge, those materials can provide properties that are highly desirable for an IOL cartridge, particularly the nozzle of the cartridge. Moreover, those materials are also quite desirable for use with a polyurethane matching polymer material of the coating since such a coating is able to directly adhere and/or bond with the surface of IOL cartridge. This allows for the coating to be applied as a single layer and one or more layers and/or one or more application steps of conventional IOL coatings can be avoided. For example, at least one conventional IOL coating required that the internal surface of the cartridge be plasma treated and that a base coat be applied to the internal surface before application of the desired coating. Using the preferred single layer coating the base coat and, even possibly the plasma treatment, become superfluous.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

We claim:

1. An IOL delivery device, the device comprising:
   a delivery cartridge having a body portion and a nozzle, the nozzle having an inner diameter and an outer diameter, the body portion and nozzle including an internal surface defining a lumen extending along the body portion and the nozzle wherein the cartridge, including the internal surface, is formed of a singular polymer material and that singular polymer material is a polyurethane material; and
   a coating disposed over the internal surface wherein the coating is formed of a polyurethane material and a hydrophilic material;
   wherein the inner diameter, the outer diameter or both of the nozzle is less than 2.5 mm and wherein the polyurethane material of the cartridge exhibits a flexural modulus that is at least 1200 MPa.

2. A device as in claim 1 wherein the coating consists essentially of the polyurethane material of the coating and the hydrophilic material.

3. A device as in claim 1 wherein the hydrophilic material includes polyvinylpyrrolidone.

4. A device as in claim 1 wherein the polyurethane material of the coating forms a cross-linked or linear matrix and the hydrophilic material is dispersed throughout the matrix.

5. A device as in claim 1 wherein the coating is a single layer disposed directly over the internal surface of the cartridge without any coating layers over the single layer.

6. A device as in claim 1 wherein the coating is disposed directly over the internal surface without any base coat between the coating and the internal surface.

7. A device as in claim 1 wherein the singular polymer material is a blend of polymers or a copolymer.

8. A device as in claim 1 wherein the coating further includes a cross-linker.

9. A device as in claim 1 wherein the material of the internal surface exhibits a hardness of at least 75D.

10. A device as in claim 9 wherein the hardness is less than 100D.

11. A device as in claim 1 wherein the ratio of the polyurethane material to hydrophilic polymer in the coating, by weight, is between about 10:1 and about 1:10.

12. A device as in claim 1 wherein the hydrophilic material is or includes polyvinylpyrrolidone (PVP) and the PVP has a K value between about 80 and 110 and the PVP has an average molecular weight that is at least 800,000 Daltons and is less than about 1.8 M.

13. A device as in claim 1 wherein the inner diameter, the outer diameter or both of the nozzle is less than 1.9 mm.

14. A device as in claim 1 wherein the polyurethane material that forms the internal surface of the cartridge has at least 70% the same monomeric repeat units, oligomeric repeat units or both as the polyurethane material that forms the coating.

15. An IOL delivery device, the device comprising:
    a delivery cartridge having a body portion and a nozzle, the nozzle having an inner diameter and an outer diameter, the body portion and nozzle including an internal surface defining a lumen extending along the body portion and the nozzle wherein the cartridge, including the internal surface, is formed of a singular polymer material and that singular polymer material is a polyurethane material; and
    a coating disposed over the internal surface wherein the coating is formed of a polyurethane material and a hydrophilic material;
    wherein the polyurethane material of the cartridge exhibits a flexural modulus that is at least 2000 MPa; and
    wherein the inner diameter, the outer diameter or both of the nozzle is less than 2.5 mm.

16. A device as in claim 15 wherein the flexural modulus is less than 3000 MPa.

17. A device as in claim 15 wherein the inner diameter, the outer diameter or both of the nozzle is less than 1.9 mm.

18. An IOL delivery device, the device comprising:
    a delivery cartridge having a body portion and a nozzle, the nozzle having an inner diameter and an outer diameter, the body portion and nozzle including an internal surface defining a lumen extending along the body portion and the nozzle wherein the cartridge, including the internal surface, is formed of a singular polymer material and that singular polymer material is a polyurethane material; and
    a coating disposed over the internal surface wherein the coating is formed of a polyurethane material and a hydrophilic material;

wherein the coating is a single layer disposed directly over the internal surface of the cartridge without any coating layers over the single layer and the coating is disposed directly over the internal surface without any base coat between the coating and the internal surface; and wherein the inner diameter, the outer diameter or both of the nozzle is less than 2.5 mm and wherein the polyurethane material of the internal surface exhibits a flexural modulus that is at least 1200 MPa.

19. A device as in claim 18 wherein the material of the Internal surface exhibits a hardness of at least 75D.

20. A device as in claim 18 wherein the inner diameter, the outer diameter or both of the nozzle is less than 1.9 mm.

21. A device as in claim 18 wherein the polyurethane material that forms the internal surface of the cartridge has at least 70% the same monomeric repeat units, oligomeric repeat units or both as the polyurethane material that forms the coating.

* * * * *